US011246544B2

(12) United States Patent
Hou et al.

(10) Patent No.: US 11,246,544 B2
(45) Date of Patent: Feb. 15, 2022

(54) SCANNING TABLE AND MEDICAL IMAGING EQUIPMENT INCLUDING SCANNING TABLE

(71) Applicant: Neusoft Medical Systems Co., Ltd., Liaoning (CN)

(72) Inventors: Guitang Hou, Shenyang (CN); Feng Shi, Shenyang (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 329 days.

(21) Appl. No.: 16/352,237

(22) Filed: Mar. 13, 2019

(65) Prior Publication Data
US 2019/0282187 A1 Sep. 19, 2019

(30) Foreign Application Priority Data
Mar. 13, 2018 (CN) .......................... 201810206264.0

(51) Int. Cl.
*A61B 6/04* (2006.01)
*A61B 5/055* (2006.01)
(Continued)

(52) U.S. Cl.
CPC ............ *A61B 6/0471* (2013.01); *A61B 5/055* (2013.01); *A61B 5/704* (2013.01); *A61B 6/0407* (2013.01); *A61G 13/02* (2013.01); *A61G 2210/50* (2013.01)

(58) Field of Classification Search
CPC ....... A61B 5/055; A61B 5/704; A61B 6/0407; A61B 6/0471; A61B 6/0487; A61G 2210/50
See application file for complete search history.

(56) References Cited

U.S. PATENT DOCUMENTS 3,588,500 A * 6/1971 Koerner ............... A61B 6/0487
5/601
5,413,523 A 5/1995 Tsai
(Continued)

FOREIGN PATENT DOCUMENTS

CN 201438964 4/2010
CN 202776341 3/2013
(Continued)

OTHER PUBLICATIONS

CN Office Action in Chinese Appln. No. 201810206264.0, dated Nov. 23, 2020, 14 pages (with English Translation).
(Continued)

*Primary Examiner* — David R Hare
*Assistant Examiner* — Alexis Felix Lopez
(74) *Attorney, Agent, or Firm* — Fish & Richardson P.C.

(57) ABSTRACT

A scanning table includes an upper pallet, a lower pallet, a support device, a driving device, an opening belt and an endless belt. The opening belt is fixedly coupled with the lower pallet. The endless belt is fixedly coupled with the upper pallet. A front end of the opening belt is provided with a first driving wheel coupled to the driving device. The lower pallet is driven by the first driving wheel to move in a front-back direction relative to the support device. The endless belt is sleeved on the lower pallet. When the lower pallet moves in the front-back direction relative to the support device, the endless belt moves synchronously with the lower pallet to drive the upper pallet to move in the same direction back and forth relative to the lower pallet.

20 Claims, 5 Drawing Sheets

(51) Int. Cl.
*A61B 5/00* (2006.01)
*A61G 13/02* (2006.01)

(56) References Cited

U.S. PATENT DOCUMENTS

| | | | | |
|---|---|---|---|---|
| 7,634,827 | B2* | 12/2009 | Gagneur | A61B 5/055 5/601 |
| 7,874,030 | B2* | 1/2011 | Cho | G01R 33/481 5/601 |
| 8,931,125 | B2* | 1/2015 | Fang | A61B 6/0471 5/601 |
| 10,130,315 | B2 | 11/2018 | Hou et al. | |
| 2007/0086577 | A1* | 4/2007 | Kobayashi | A61B 6/0487 378/195 |
| 2007/0143921 | A1* | 6/2007 | Hiyama | A61B 5/055 5/601 |
| 2007/0226906 | A1* | 10/2007 | Farooqui | A61B 6/0487 5/601 |
| 2007/0272105 | A1 | 11/2007 | Burgess et al. | |
| 2008/0045831 | A1 | 2/2008 | Cho et al. | |
| 2008/0098525 | A1* | 5/2008 | Doleschal | A61B 6/547 5/600 |
| 2011/0047700 | A1* | 3/2011 | Klemm | A61B 6/0487 5/600 |
| 2013/0176029 | A1* | 7/2013 | Oosawa | A61B 5/055 324/321 |
| 2014/0187379 | A1* | 7/2014 | Chen | A61B 6/0487 477/12 |
| 2014/0208509 | A1* | 7/2014 | Zhang | A61B 6/0407 5/601 |

FOREIGN PATENT DOCUMENTS

| | | |
|---|---|---|
| CN | 103027817 A | 4/2013 |
| CN | 103565434 | 2/2014 |
| CN | 203662786 | 6/2014 |
| CN | 204744172 | 11/2015 |
| CN | 105380674 | 3/2016 |
| CN | 205829375 | 12/2016 |
| WO | WO-2008049166 A1 * | 5/2008 ........... A61B 6/0487 |

OTHER PUBLICATIONS

Office Action and Search Report in Chinese Appln. No. 201810206264.0, dated May 18, 2021. 16 pages (with Partial Machine Translation).
Office Action and Search Report in Chinese Appln. No. 201810206264.0, dated Aug. 20, 2021, 21 pages (with Machine Translation).

* cited by examiner

SCANNING TABLE AND MEDICAL IMAGING EQUIPMENT INCLUDING SCANNING TABLE

CROSS REFERENCE TO RELATED APPLICATIONS

This application claims priority to Chinese Patent Application No. 201810206264.0 filed on Mar. 13, 2018, the entire content of which is incorporated herein by reference.

TECHNICAL FIELD

The present relates to scanning tables and medical imaging equipment including the scanning tables in the medical imaging field.

BACKGROUND

In the diagnosis process of some diseases in patients, a variety of different imaging technologies may be used to scan and image the patients, so as to assist the diagnosis. Those imaging technologies may include MRI (Magnetic Resonance Imaging), CT (Computed Tomography), PET (Positron Emission Tomography), etc., and relevant medical imaging equipment usually includes a scanning table to support the patient.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in long medical equipment, NMS has been committed to the study of avoiding secondary potential harm caused by excessive X-ray irradiation to the subject during the CT scanning process.

SUMMARY

The present disclosure provides scanning tables and medical imaging devices or systems including such scanning tables, which can implement long distance back and forth movement.

One aspect of the present disclosure features scanning table including: an upper pallet configured to support a subject; a lower pallet; a support device configured to support the upper pallet and the lower pallet; a driving device configured to drive the upper pallet and the lower pallet to move in a front-back direction; an opening belt configured to drive the lower pallet to move in the front-back direction relative to the support device; and an endless belt configured to drive the upper pallet to move in the front-back direction relative to the lower pallet. The opening belt is fixedly coupled with the lower pallet, and the endless belt is fixedly coupled with the upper pallet. A front end of the opening belt is provided with a first driving wheel coupled to the driving device and an axis of the first driving wheel is in a left-right direction of the scanning table, and the lower pallet is driven by the first driving wheel to move in the front-back direction relative to the support device. The endless belt is sleeved on the lower pallet and configured to, when the lower pallet moves in the front-back direction relative to the support device, move synchronously with the lower pallet to drive the upper pallet to move in the same direction back and forth relative to the lower pallet.

In some implementations, the driving device includes: a reversing device; a power component disposed at a back end of the scanning table; and a transmission shaft disposed along the front-back direction, an axis of the transmission shaft being along the front-back direction. A back end of the transmission shaft is coupled to the power component, and a front end of the transmission shaft is coupled to the reversing device, and a power is transmitted to the first driving wheel by the reversing device.

In some examples, the reversing device includes: a second driving wheel and a third driving wheel cooperated with the second driving wheel. An axis of the second driving wheel is in the left-right direction of the scanning table and is coupled circumferentially with the first driving wheel, and an axis of the third driving wheel is in the front-back direction and is coupled to the front end of the transmission shaft. Both of the second driving wheel and the third driving wheel can be spiral bevel gears or straight tooth bevel gears.

In some examples, the reversing device includes a right angle reducer.

In some implementations, the scanning table further includes: a front connector fixedly coupled with the front end of the opening belt and a back connector fixedly coupled with a back end of the opening belt. The front connector is ahead of the first driving wheel along the front-back direction. A front end of the lower pallet can be fixedly coupled with the front connector, and a back end of the lower pallet can be fixedly coupled with the back connector.

In some examples, the opening belt includes a front opening belt located in front of the first driving wheel and a back opening belt located behind the first driving wheel, and the front opening belt and the back opening belt are disposed in a same plane above the first driving wheel. The front connector can be fixedly coupled to a front end of the front opening belt, and the back connector can be fixedly coupled to a back end of the back opening belt.

The scanning table can further include: a first transmission wheel above the first driving wheel, the first transmission wheel being located below the opening belt and configured to guide the front opening belt to extend upward; and a second transmission wheel above the first driving wheel, the second transmission wheel being located below the opening belt and configured to guide the back opening belt to extend upward. The first driving wheel can be located between the first transmission wheel and the second transmission wheel and above a portion of the opening belt that is between the front opening belt and the back opening belt.

The endless belt can be coupled with a first connector fixed on the support device. A lower part of the endless belt can be fixedly coupled to the support device by the first connector, and an upper part of the endless belt can be fixedly coupled to the upper pallet by a second connector. The first connector can be disposed at a front end of the lower part of the endless belt, and the second connector can be disposed at a back end of the upper part of the endless belt.

In some implementations, the scanning table further includes: a third transmission wheel hinged at a front end of the lower pallet; and a fourth transmission wheel hinged at a back end of the lower pallet. A hinge shaft of the third transmission wheel and a hinge shaft of the fourth transmission wheel can be in the left-right direction of the scanning table, and the endless belt can be sleeved on the third transmission wheel and the fourth transmission wheel.

The opening belt can include a synchronous belt or a chain, and the first driving wheel can include a synchronous pulley or a chain wheel. The endless belt can include a synchronous belt or a chain, and both of the third transmission wheel and the fourth transmission wheel can be synchronous pulleys or chain wheels.

A length of the opening belt can be substantially half of a length of the endless belt.

Another aspect of the present disclosure features a medical imaging system. The medical imaging system includes an imaging device configured to scan a region of interest of a subject and a scanning table configured to support the subject. The scanning table can include one or more features of the scanning table as described above.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
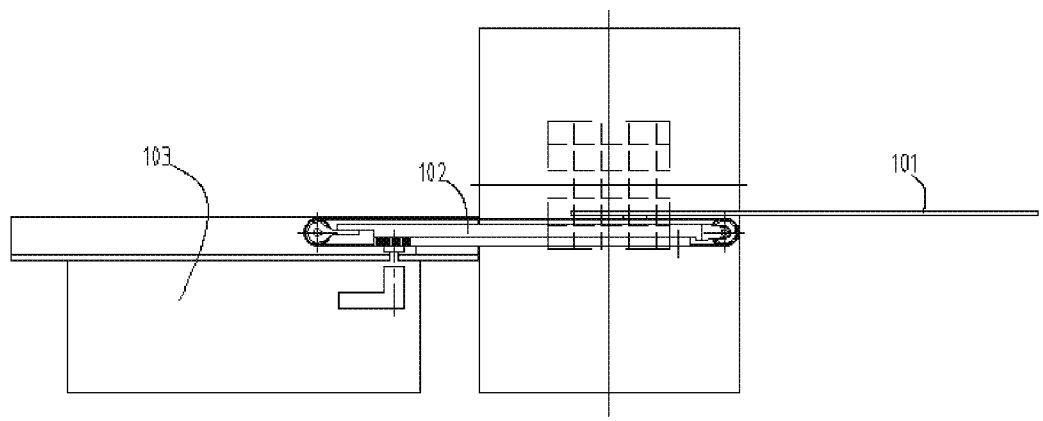
FIG. 1 is a structure diagram illustrating an upper pallet of a scanning table in medical imaging equipment at a maximum distance position according to one or more examples.

The present disclosure will be specifically described below in conjunction with the accompanying drawings, so that those skilled in the art may accurately understand the technical solutions of the present disclosure.

Up, down, left and right directions described herein are based on a normal use state of medical imaging equipment. The term "medical imaging equipment" herein can be used interchangeably with "medical image device" or "medical image system". During the process of using the medical imaging equipment, a direction perpendicular to a ground is an up and down direction, a direction of vertically pointing to the ground is downward, and a direction vertically away from the ground is upward. A length direction of the scanning table is a front-back direction. In the length direction of the scanning table, a direction towards an imaging device of the medical imaging equipment is forward, and a direction away from the imaging device is backward. The scanning table may be sent into the imaging device from back to front and retracted to a support device from front to back. In a plane parallel to the scanning table, a direction perpendicular to the front-back direction is a left-right direction, that is, a width direction of the scanning table is the left-right direction. When a subject lies on the scanning table, the direction of the left hand of the subject is left, and the direction of the right hand of the subject is right.

The terms first, second, third and so on used herein are used to distinguish two or more components that are identical or similar in structure, or two or more structures that are identical or similar, and do not represent a particular limitation of the order.

The medical imaging equipment includes a scanning table for supporting a subject. The medical imaging equipment can include, but not limited to, MRI equipment, CT imaging equipment, PET imaging equipment, and X-ray imaging equipment. MRI equipment is exemplified below to describe a scanning table of the medical imaging equipment.

MRI equipment is widely used in medical clinical and scientific research, and includes a magnet, a gradient coil, a radio frequency (RF) transmitting coil, a RF receiving coil, and a scanning table for supporting a subject. The scanning table is configured to move the subject to a main magnetic field and a gradient field generated by the magnet and the gradient coil. The RF transmitting coil is configured to excite the subject to generate magnetic resonance signals. The RF receiving coil is configured to receive the generated magnetic resonance signals and sends them to a computer. The computer is configured to reconstruct a magnetic resonance image based on the generated magnetic resonance signals. If a whole body scan of the subject is to be performed in the MRI equipment based on one-time positioning (one posture lying on the scanning table), a pallet of the scanning table is to have a moving distance of 2,800 mm or even 3,000 mm.

Limited by the installation space of the MRI equipment and the structure of the scanning table, in an example, the scanning table includes a double-layer pallet structure and a horizontal driving device including a power source. The double-layer pallet structure includes an upper pallet for supporting the subject and a lower pallet. The lower pallet is driven by the power source to move horizontally in the front-back direction, so as to form a first-stage drive. The upper pallet is driven by the lower pallet to move horizontally in the same direction as the lower pallet, so as to form a second-stage drive, thereby implementing long distance back and forth movement of the upper pallet of the scanning table.

Figure 2:
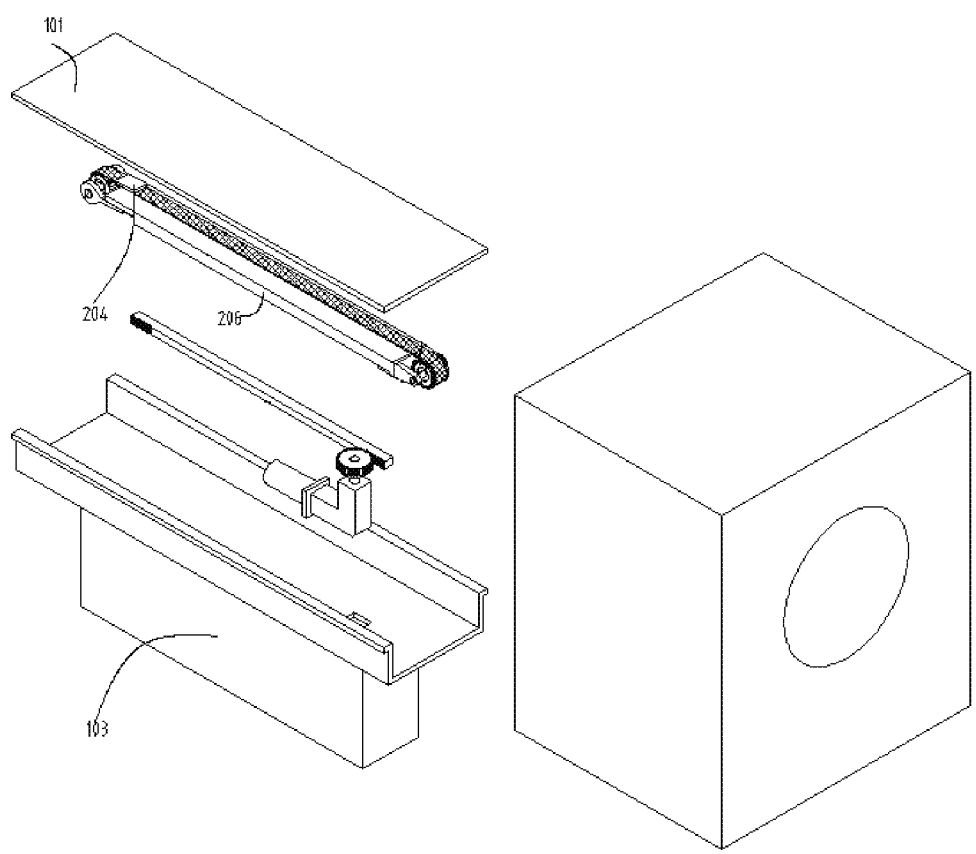
FIG. 2 is an exploded view of the structure shown in FIG. 1.

FIG. 1 is a structure diagram illustrating an upper pallet of a scanning table in medical imaging equipment at a maximum distance position according to one or more examples. FIG. 2 is an exploded view of the structure shown in FIG. 1.

A scanning table of the medical imaging equipment shown in FIG. 1 and FIG. 2 includes an upper pallet 101, a lower pallet 206, a scanning table support device 103, a driving device 102 and an upper pallet connector 204, so as to implement long distance back and forth movement of the upper pallet of the scanning table. The driving device 102 includes a driving motor. The driving motor drives the lower pallet 206 to horizontally move back and forth relative to the scanning table support device 103 via gears. The upper pallet connector 204 drives the upper pallet 101 to move in the same direction as the lower pallet 206 relative to the lower pallet 206, which is equivalent to the upper pallet 101 horizontally moving back and forth with double distance relative to the scanning table support device 103, to implement long distance back and forth movement of the upper pallet of the scanning table.

Figure 3:
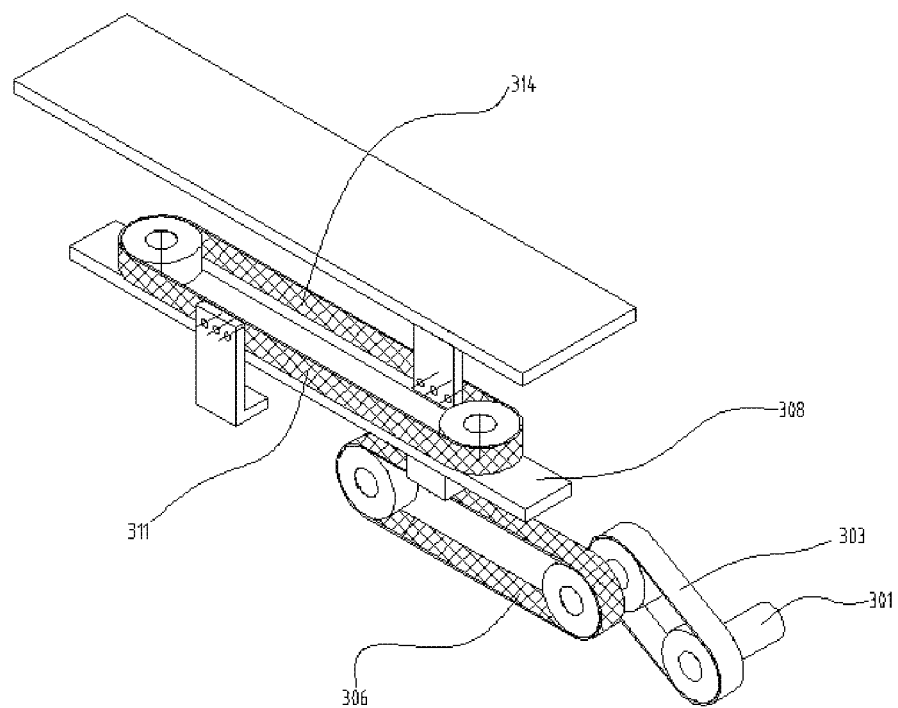
FIG. 3 is a schematic diagram illustrating a driving manner of a scanning table in medical imaging equipment according to one or more examples.

FIG. 3 is a schematic diagram illustrating a driving manner of a scanning table in medical imaging equipment according to one or more examples.

As shown in FIG. 3, the driving motor 301 drives a first transmission belt 303 and a second transmission belt 306 to move through transmission wheels, such that the second transmission belt 306 drives a lower pallet 308 to move back and forth. A connecting board coupled with a side of a third transmission belt 311 is fixedly connected to a support device horizontally stationary relative to the ground, and thus the third transmission belt 311 moves back and forth relative the lower pallet 308. In this way, the upper pallet 314 is driven to horizontally move back and forth in the same direction as the lower pallet 308, thereby implementing long distance back and forth movement of the upper pallet of the scanning table.

Figure 4:
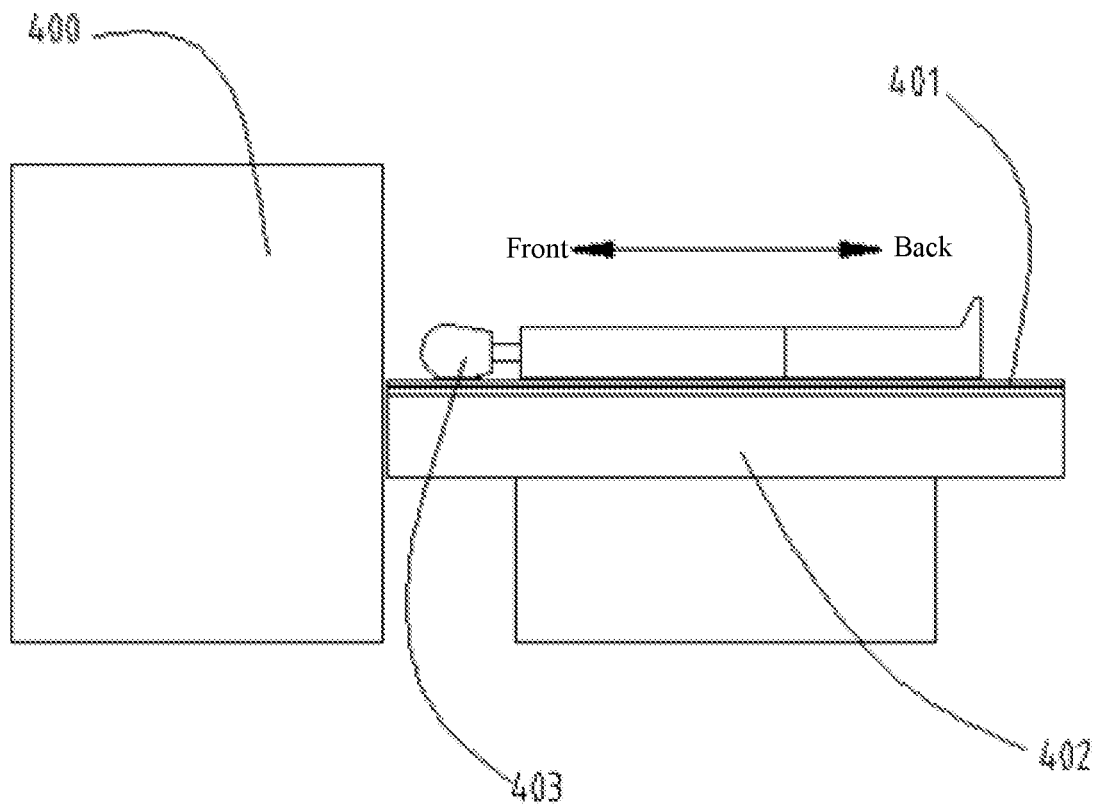
FIG. 4 is a structure diagram illustrating medical imaging equipment according to one or more examples of the present disclosure.

FIG. 4 is a structure diagram illustrating medical imaging equipment according to one or more examples of the present disclosure. As shown in FIG. 4, the medical imaging equipment includes an imaging device and a scanning table. The scanning table is configured to support a subject and capable of transmitting the subject into the imaging device, so as to obtain an image of a region of interest of the subject or treat the region of interest of the subject. The imaging device is configured to scan the region of interest of the subject. If the scanning table moves a sufficiently long distance, the whole body of the subject may be placed successively in an imaging scope, so that the whole body scan can be completed with once positioning of the subject. In the actual clinical examination, taking MRI as an example, if it is desired to obtain a whole body image of the subject, an image of each part of the subject is respectively reconstructed in a case that the position/posture of the subject remains unchanged. The whole body image of the subject is then obtained by combining the reconstructed image of each part together. It is noted that if the position/posture of the subject changes when collecting magnetic resonance signals of each part, the reconstructed image of each part cannot be combined, and in this case, the whole body image of the subject cannot be obtained. Therefore, to ensure that the whole body scan can be completed with one-time positioning of the subject, the scanning table may move a sufficiently long distance.

The imaging device may be a magnet 400, and may be an imaging device used in other medical fields such as CT or PET.

As shown in FIG. 4, the scanning table includes a support device 402 and a driving device 401 for driving the pallet to move back and forth relative to the support device. A subject 403 may be placed on the scanning table. The scanning table can be similar to the scanning table of FIGS. 1 and 2 or the scanning table of FIG. 3.

Figure 5:
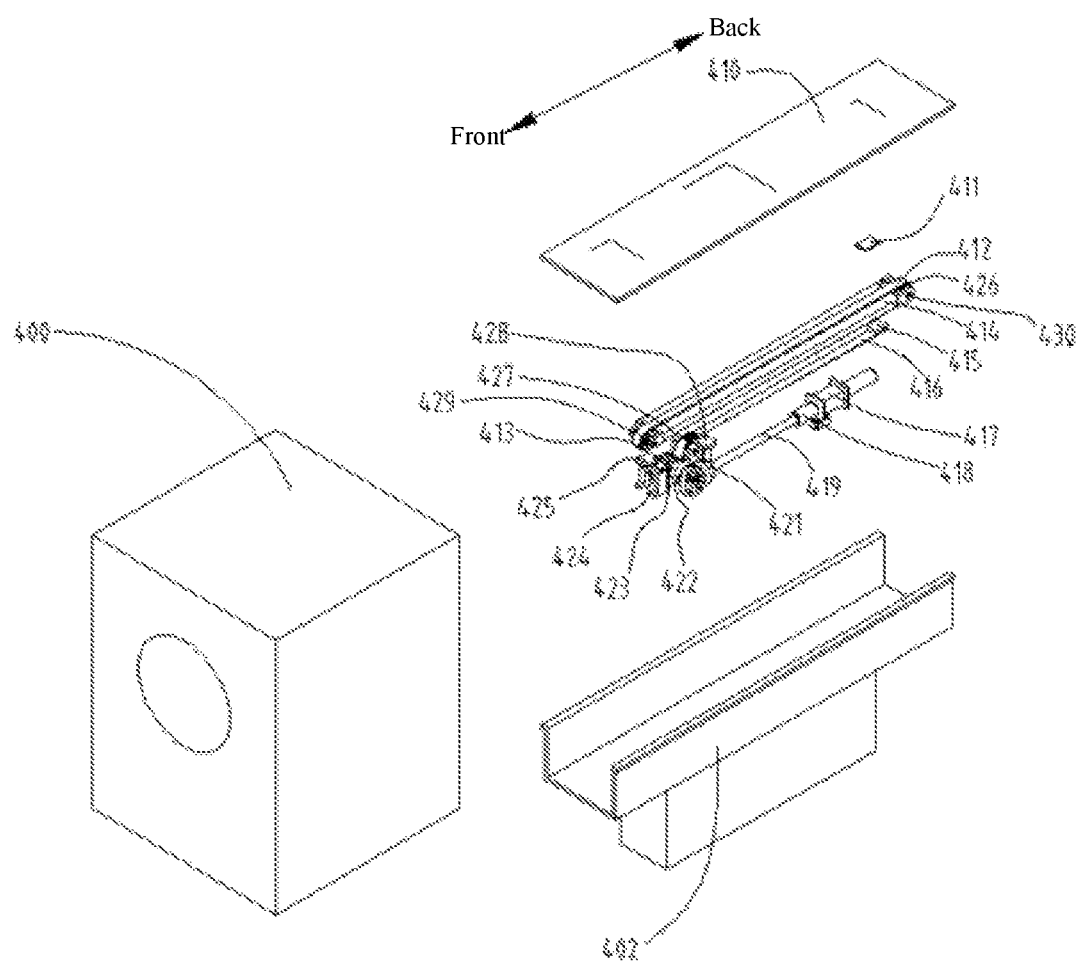
FIG. 5 is an exploded view of the scanning table of the medical imaging equipment shown in FIG. 4.

As shown in FIG. 5, the scanning table provided by the present disclosure can include a support device 402, a driving device 401, an upper pallet 410, a lower pallet 414, an opening belt 416, and an endless belt 412. The support device 402 forms the basis of the scanning table and is used for supporting the upper pallet 410 and the lower pallet 414. The upper pallet 410 and the lower pallet 414 may be coupled with the support device 402 in a rollable or slidable manner (or configuration). The driving device 401 is configured to drive the upper pallet 410 to move along the front-back direction relative to the support device 402, so that the upper pallet 410 is driven to move forwardly into a scanning bore of the imaging device, and after the scanning for the subject is completed, the upper pallet 410 is driven to move away from the scanning bore and back to the support device 402. In an example, the opening belt 416 is fixedly coupled to the lower pallet 414 and the endless belt 412 is fixedly coupled to the upper pallet 410. In this way, the moving directions of the opening belt 416 and the endless belt 412 are the same as those of the upper pallet 410 and the lower pallet 414, respectively. The opening belt 416 is configured to drive the lower pallet 414 to move back and forth relative to the support device 402. The endless belt 412 is configured to drive the upper pallet 410 to move back and forth relative to the lower pallet 414. The opening belt 416 refers to a belt without an enclosed space. For example, an opening belt can be obtained by cutting an endless belt.

The scanning table may include components for performing back and forth movement except the support device 402 and the subject 403. The components can include one or more of the driving device 401, the upper pallet 410, the lower pallet 414, the opening belt 416, the endless belt 412, and the like.

Figure 6:
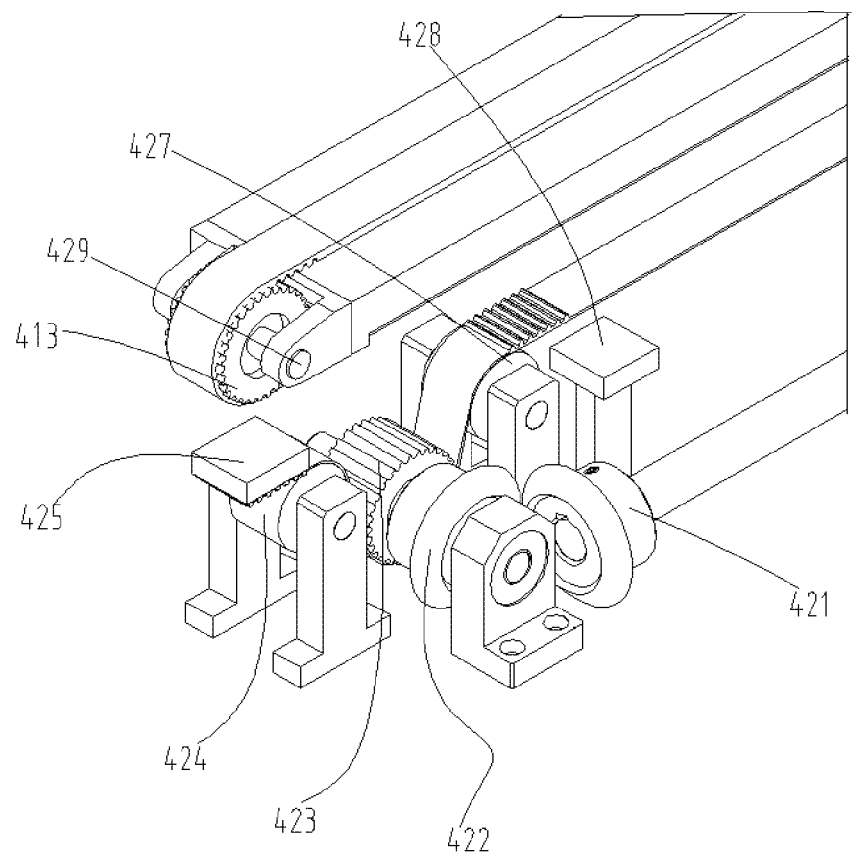
FIG. 6 is an enlarged view of a front transmission structure of the scanning table shown in FIG. 5.

As shown in FIG. 6, a front end of the opening belt 416 is provided with a first driving wheel 423 coupled with the driving device 401. A power component, such as a driving motor in the driving device 401, may be disposed at a back end of the scanning table and mounted on the support device 402. An axis of the first driving wheel 423 is in the left-right direction of the scanning table. The driving device 401 transmits power to the first driving wheel 423, so as to drive the first driving wheel 423 to rotate about its axis. This rotation may be translated into the movement of the opening belt 416 in the front-back direction. Since the lower pallet 414 is fixed coupled to the opening belt 416, when the opening belt 416 is driven to move in the front-back direction, the lower pallet 414 is driven to move in the front-back direction relative to the support device 402.

In some examples, the endless belt 412 is sleeved on the lower pallet 414. The endless belt 412 may be coupled with a first connector 428 fixedly installed on the support device 402. As the lower pallet 414 is driven to move back and forth relative to the support device 402, the endless belt 412 is driven to move back and forth along with the lower pallet 414 since the endless belt 412 is sleeved on the lower pallet 414. A portion of the endless belt 412 is fixedly coupled to the support device 402 by the first connector 428, and thus, when the lower pallet 414 is driven to move back and forth relative to the support device 402, the endless belt 412 is driven to rotate in the rotating direction of the endless belt 412 relative to the lower pallet 414. In this process, the portion of the endless belt 412 coupled with the first connector 428 is stationary relative to the support device 402. If the lower pallet 414 is driven to move from the back to the front, an upper part of the endless belt 412 coupled with the upper pallet 410 is also driven to move from the back to the front, that is, the upper part of the endless belt 412 coupled with the upper pallet 410 moves synchronously with the lower pallet 414, thereby driving the upper pallet 410 to move synchronously in the front-back direction. In this way, the long distance back and forth movement of the upper pallet 410 relative to the support device 402 can be implemented.

To implement the long distance back and forth movement of the upper pallet 410 relative to the support device 402, the scanning table provided by the present disclosure is provided with a double-layer pallet structure. The double-layer pallet structure includes the upper pallet 410 and the lower pallet 414. The upper pallet 410 is coupled with the support device 402 by the lower pallet 414. The driving device drives the lower pallet 414 to move in the front-back direction relative to the support device 402. The lower pallet 414 further drives the upper pallet 410 to move in the front-back direction relative to the lower pallet 414. In this way, a back and forth moving distance of the upper pallet 410 relative to the support device 402 is equal to a sum of a back and forth moving distance of the upper pallet 410 relative to the lower pallet 414 and a back and forth moving distance of the lower pallet 414 relative to the support device 402. In this way, the upper pallet 410 is not too long, the deflection of the upper pallet 410 is not increased because the length of the upper pallet 410 is not increased, the support stability of the upper pallet 410 is improved, and the long distance back and forth movement of the upper pallet 410 is implemented while satisfying scanning requirements.

In addition, single-stage driving of the opening belt 416 is applied in the driving device. The lower pallet 414 is driven by the first driving wheel 423 cooperated with the opening belt 416. At this time, on one hand, the opening belt 416 is rigider than the endless belt 412, the gap control is more accurate and the transmission precision can be improved; and on the other hand, since the transmission precision of a belt is inversely proportional to its length, the length of the opening belt 416 is substantially half of the endless belt 412, which greatly improves the transmission precision. Furthermore, the length of the transmission belt is not excessively long due to the reliability of the transmission, and the more the transmission stages, the lower the transmission precision. Therefore, in the present disclosure, the opening belt 416 is directly driven by the first driving wheel 423 coupled with the driving device, thereby effectively shortening the number of transmission stages and improving the transmission precision.

FIG. 5 is an exploded view of the scanning table of the medical imaging equipment shown in FIG. 4. FIG. 6 is an enlarged view of a front transmission structure of the scanning table shown in FIG. 5. As shown in FIGS. 5 and 6, the driving device includes a reversing mechanism (or a reversing device), a power component 417 disposed at a back end of the scanning table, and a transmission shaft 419 disposed along the front-back direction, that is, an axis of the transmission shaft is along the front-back direction. The axis of the first driving wheel 423 is in the left-right direction of the scanning table, a back end of the transmission shaft 419 is coupled to the power component 417, and a front end of the transmission shaft 419 is coupled to the reversing mechanism. In this way, the power can be transmitted to the first driving wheel 423 by the reversing mechanism. The power component 417 drives the transmission shaft 419 to rotate about its axis, and the rotation is transmitted to the first driving wheel 423 by the reversing mechanism, and finally the first driving wheel 423 drives the opening belt 416 to move in the front-back direction.

The power component 417 may include an electric motor, or include a combination of an electric motor and a speed reducer. The power component 417 may be a ferromagnetic component. The power component 417 may be coupled to the transmission shaft 419 by a coupling device (or coupler) 418. Or the power component 417 may directly drive the transmission shaft 419.

As shown in FIG. 6, the reversing mechanism may include a second driving wheel 422 and a third driving wheel 421 cooperated with the second driving wheel. An axis of the second driving wheel 422 is in the left-right direction of the scanning table and is coupled circumferentially with the first driving wheel 423. That is, the second driving wheel 422 is disposed coaxially with the first driving wheel 423. An axis of the third driving wheel 421 is in the front-back direction and is fixedly coupled to the front end of the transmission shaft 419. When the transmission shaft 419 is rotated circumferentially under the driving of the power component 417, the third driving wheel 421 is synchronously rotated, the rotation of the third driving wheel 421 drives the second driving wheel 422 to rotate, the rotation of the second driving wheel 422 drives the first driving wheel 423 to rotate, and the rotation of the first driving wheel 423 drives the opening belt 416 to move in the front-back direction.

Therefore, by the reversing mechanism and the transmission shaft 419, the power component 417 may be disposed at the back end of the scanning table and away from the first driving wheel 423 on the opening belt 416. Due to the limitation of the driving manner, to implement the long distance movement of the opening belt 416 from the back to the front, so that the lower pallet 414 is driven forward into the imaging device by the opening belt 416, the first driving wheel 423 is disposed at the front end of the opening belt 416, that is, the first driving wheel 423 is disposed close to the imaging device. However, as described above, the power component 417 is the ferromagnetic component, and the imaging device includes a magnetic component such as the magnet 400. If the power component 417 is disposed close to the imaging device, the uniformity of the magnetic field and the linearity of the gradient field can be affected. Therefore, by the reversing mechanism and the transmission shaft 419, the power component 417 is disposed at the back end of the scanning table and away from the imaging device, thereby avoiding affecting the imaging device.

The second driving wheel 422 and the third driving wheel 421 may both be spiral bevel gears, or may both be straight tooth bevel gears, to improve transmission reliability and meet the reversing demand. That is, if the second driving wheel 422 is a spiral bevel gear, the third driving wheel 421 is also a spiral bevel gear; and if the second driving wheel 422 is a straight tooth bevel gear, the third driving wheel 421 is also a straight tooth bevel gear. Those skilled in the art may select other types of driving wheels as the second driving wheel 422 and the third driving wheel 421 as needed.

It is understood that, in view of the direction in which the first driving wheel 423 and the transmission shaft 419 are substantially at a right angle to each other, the reversing mechanism in the present disclosure may also be a right angle reducer. One end of the right angle reducer is coupled to the transmission shaft 419, and the other end of the right angle reducer is coupled to the first driving wheel 423.

As shown in FIGS. 5 and 6, the front and back ends of the opening belt 416 may be respectively fixedly coupled with a front connector 425 and a back connector 415. The front connector 425 is before (or ahead of) the first driving wheel 423 along the front-back direction. The front end of the lower pallet 414 is fixedly coupled with the front connector 425. The back end of the lower pallet 414 is fixedly coupled with the back connector 415. In this way, the lower pallet 414 is fixedly coupled with the opening belt 416.

The front connector 425 and the back connector 415 may be disposed in accordance with the structure of the opening belt 416. For example, the opening belt 416 is a synchronous belt or a chain, and the first driving wheel 423 is correspondingly a synchronous pulley or a chain wheel, and both the front connector 425 and the back connector 415 are cooperated with the opening belt 416.

In some examples, the scanning table further includes a first transmission wheel 424 and a second transmission wheel 427 respectively on the front and back sides of the first driving wheel 423. Both the first transmission wheel 424 and the second transmission wheel 427 are disposed above the first driving wheel 423 and under/below the opening belt 416 to respectively guide the front and back portions of the opening belt 416 to extend upward, such that the front and back portions of the opening belt 416 are above the first driving wheel 423. The front portion of the opening belt 416 before the first driving wheel 423 is referred to as a front opening belt. The back portion of the opening belt 416 after the first driving wheel 423 is referred to as a back opening belt. At this case, the front connector 425 is fixedly coupled to a front end of the front opening belt, and the back connector 415 is fixedly coupled to a back end of the back opening belt. The first driving wheel 423 is positioned above a portion of the opening belt 416 that is between the front opening belt and the back opening belt. That is, the opening belt 416 has a concave shape with the portion of the opening belt below the first driving wheel 423 and the front opening belt and the back opening belt in a plane above the first driving wheel 423.

By the first transmission wheel 424 and the second transmission wheel 427, the rotation of the first driving wheel 423 is converted into a linear movement of the opening belt 416 in the front-back direction, so as to drive the lower pallet 414 to move in the front-back direction. Moreover, the first transmission wheel 424 and the second transmission wheel 427 are disposed higher than the first driving wheel 423, so that "sinking" mounting of the first driving wheel 423 may be implemented. In this way, the first driving wheel 423 is prevented from protruding upward and colliding against the lower pallet 414, thereby preventing the first driving wheel 423 from interfering with the lower pallet 414.

On the basis of the above, a third transmission wheel 413 and a fourth transmission wheel 426 are respectively hinged at the front and back ends of the lower pallet 414, and the endless belt 412 is sleeved on the lower pallet 414. An axis of the third transmission wheel 413 is in the left-right direction of the scanning table. An axis of the fourth transmission wheel 426 is in the left-right direction of the scanning table. In this way, the endless belt 412 may be driven by the third transmission wheel 413 and the fourth transmission wheel 426 to rotationally move in the front-back direction.

In some examples, the endless belt 412 is divided into the upper part and a lower part. The lower part of the endless belt 412 is fixedly coupled to the support device 402 by the first connector 428, and the upper part of the endless belt 412 is fixedly coupled to the upper pallet 410 by a second connector 411. The first connector 428 is disposed on a front end of the lower part the endless belt 412, and the second connector 411 is disposed at a back end of the upper part of the endless belt 412.

Those skilled in the art may set the endless belt 412 as a synchronous belt or a chain as needed. At this time, the third transmission wheel 413 and the fourth transmission wheel 426 are both provided as synchronous pulleys or chain wheels to cooperate with the endless belt 412. If the endless belt 412 is provided as a synchronous belt, the third transmission wheel 413 and the fourth transmission wheel 426 are both provided as synchronous pulleys. If the endless belt 412 is provided as a chain, the third transmission wheel 413 and the fourth transmission wheel 426 are both provided as chain wheels.

It is noted that the third transmission wheel 413 and the fourth transmission wheel 426 are not limited to synchronous pulleys and chain wheels, and the endless belt 412 is not limited to a synchronous belt and a chain. If the third transmission wheel 413, the fourth transmission wheel 426, and the endless belt 412 are defined as a group of transmission mechanism, the number of groups of transmission mechanism may be one, but not limited to one, and may be two or more.

Similarly, the first driving wheel 423 is not limited to a synchronous pulley and a chain wheel, and the opening belt 416 is not limited to a synchronous belt and a chain. If the first driving wheel 423 and the opening belt 416 are defined as a group of transmission mechanism, the number of groups of transmission mechanism may be one, but not limited to one, and may be two or more.

Further, the third driving wheel 421 and the second driving wheel 422 may be spiral bevel gears, but not limited to spiral bevel gears, or may be straight tooth bevel gears, or other forms of driving wheels.

As shown in FIGS. 5-8, in the first stage transmission, the opening belt 416 is cooperated with the first driving wheel 423, and the rotation of the first driving wheel 423 is converted into a horizontal movement of the opening belt 416 by the first transmission wheel 424 and the second transmission wheel 427. Both ends of the opening belt 416 are coupled with both ends of the lower pallet 414 by the front connector 425 and the back connector 415, respectively.

In the second stage transmission, the third transmission wheel 413 and the fourth transmission wheel 426 are hingedly fixed to both ends of the lower pallet 414 by a hinge shaft 429 and a hinge shaft 430, respectively, and the endless belt 412 is sleeved on the third transmission wheel 413 and the fourth transmission wheel 426. A portion of the upper part of the endless belt 412 close to the fourth transmission wheel 426 is coupled to the upper pallet 410 by the second connector 411. A portion of the lower part of the endless belt 412 close to the third transmission wheel 413 is coupled to the support device 402 by the first connector 428.

Figure 7:
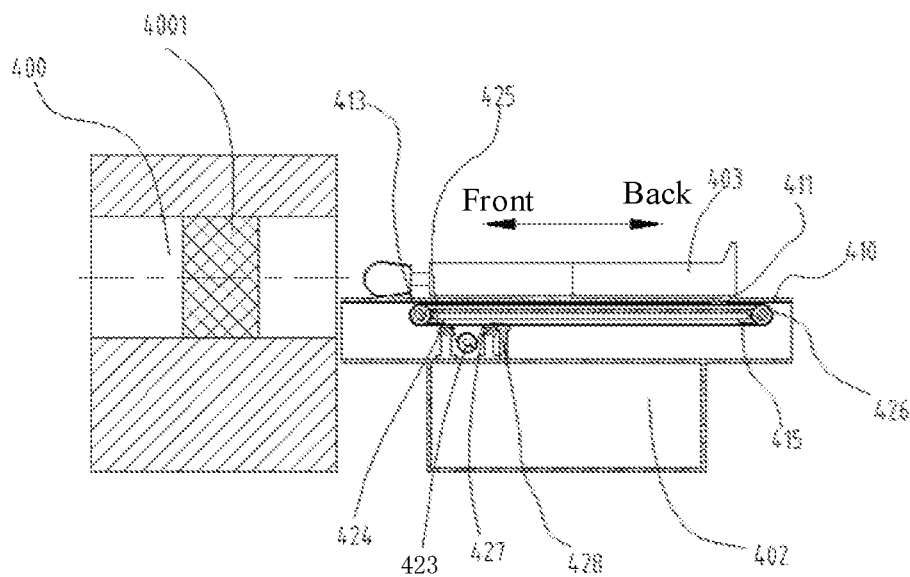
FIG. 7 is a structure diagram illustrating the scanning table in the medical imaging equipment shown in FIG. 4 at an initial position.
Figure 8:
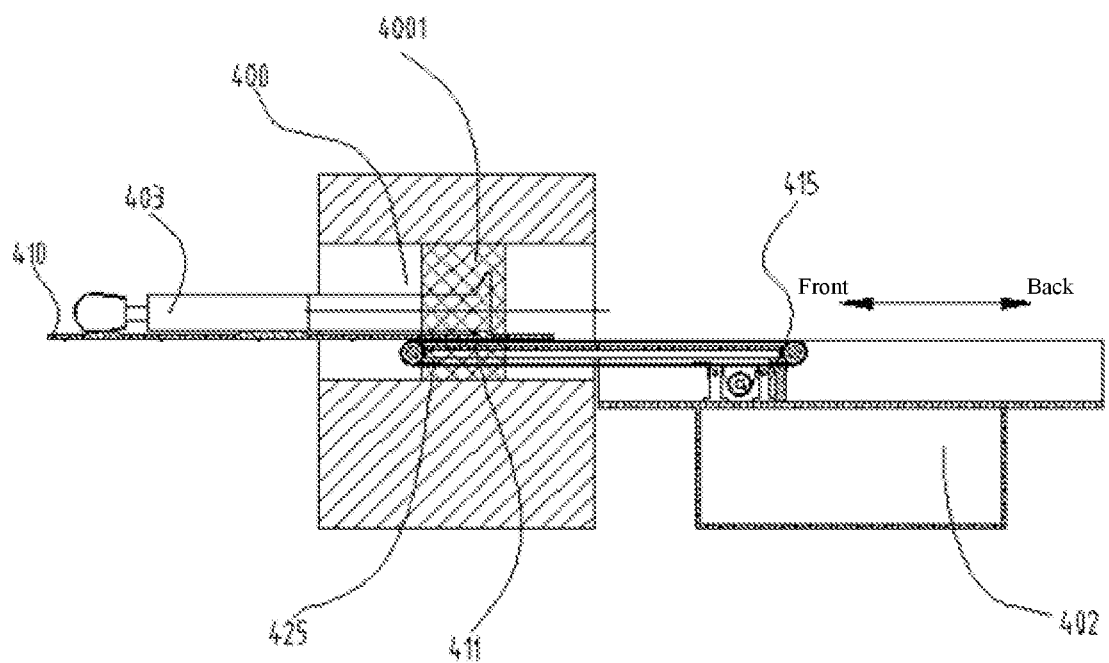
FIG. 8 is a structure diagram illustrating the scanning table in the medical imaging equipment shown in FIG. 4 at a maximum distance position.

As shown in FIGS. 7 and 8, the power component 417 drives the third driving wheel 421 to rotate by the coupling device 418 and the transmission shaft 419. The third driving wheel 421 drives the second driving wheel 422 to rotate. The second driving wheel 422 drives the first driving wheel 423 to rotate. The first driving wheel 423 drives the opening belt 416 to rotate. The opening belt 416 is further reversibly driven by the first transmission wheel 424 and the second transmission wheel 427, so as to implement the back and forth movement of the opening belt 416 in the front-back direction. At the same time, the front and back ends of the opening belt 416 drive the lower pallet 414 to move in the front-back direction by the front connector 425 and the back connector 415, and the third transmission wheel 413, the fourth transmission wheel 426 and the endless belt 412 coupled on the lower pallet 414 move back and forth in synchronization with the lower pallet 414.

Since the support device 402 and the first connector 428 fixed on the support device 402 are stationary relative to the ground, a portion of the upper part of the endless belt 412 at which the endless belt 412 is coupled with the first connector 428 is stationary relative to the ground. When the lower pallet 414 is driven to move back and forth, the third transmission wheel 413 and the fourth transmission wheel 426 fixed on the lower pallet 414 are also driven to move back and forth, and the endless belt 412 sleeved on the third transmission wheel 413 and the fourth transmission wheel 426 is also driven to move synchronously with the lower pallet 414. Since the portion of the upper part of the endless belt 412 at which the endless belt 412 is coupled with the first connector 428 is stationary relative to the ground, the portion of the upper part of the endless belt 412 at which the endless belt 412 is coupled with the first connector 428 is driven to move back and forth relative to the lower pallet 414, such that the entire endless belt 412 is driven to move back and forth relative to the lower pallet 414. The back and forth movement of the entire endless belt 412 further drives the second connector 411 fixed on the upper part of the endless belt 412 to move back and forth relative to the lower pallet 414. Finally, the second connector 411 drives the upper pallet 410 to move back and forth relative to the lower pallet 414.

According to the above motion principle, the lower pallet 414 moves back and forth relative to the support device 402 with a first distance, and the upper pallet 410 moves back and forth relative to the lower pallet 414 with a second distance. Therefore, the upper pallet 410 moves back and forth relative to the support device 402 with a sum of the first distance and the second distance. In this way, the long distance back and forth movement of the upper pallet 410 can be implemented. FIG. 7 is a structure diagram illustrating the scanning table in the medical imaging equipment shown in FIG. 4 at an initial position. FIG. 8 is a structure diagram illustrating the scanning table in the medical imaging equipment shown in FIG. 4 at a maximum distance position. The initial position is shown in FIG. 7. The maximum distance position is shown in FIG. 8. As shown in FIG. 8, the foot of the subject 403 placed on the upper pallet 410 reaches the scanning area 4001 of the magnet 400. Therefore, the whole body scanning in the MRI equipment can be implemented with the scanning table of the present disclosure.

In view of the complicated structure of the medical imaging equipment, only the scanning table is described herein. For other structures of the medical imaging equipment, please refer to the prior art, which will not be enumerated herein.

The present disclosure also provides medical imaging equipment including an imaging device and a scanning table. The scanning table is configured to move a subject into or out of the imaging device. The imaging device is configured to scan a region of interest of the subject. The specific structure of the scanning table may be referred to the above examples, and further details are omitted for brevity.

The scanning table provided by the present disclosure and the medical imaging equipment having the scanning table are described in detail above. The principles and examples of the present disclosure have been described herein with reference to some examples. The description of the above examples is only for the purpose of understanding the core concepts of the present disclosure.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

What is claimed is:

1. A scanning table comprising:
    an upper pallet configured to support a subject;
    a lower pallet;
    a support device configured to support the upper pallet and the lower pallet;
    a driving device configured to drive the upper pallet and the lower pallet to move in a front-back direction;
    an opening belt configured to drive the lower pallet to move in the front-back direction relative to the support device; and
    an endless belt configured to drive the upper pallet to move in the front-back direction relative to the lower pallet,
    wherein the opening belt is fixedly coupled with the lower pallet, and the endless belt is fixedly coupled with the upper pallet,
    wherein a front end of the opening belt is provided with a first driving wheel coupled to the driving device and an axis of the first driving wheel is in a left-right direction of the scanning table, and wherein the lower pallet is driven by the first driving wheel to move in the front-back direction relative to the support device,
    wherein the endless belt is sleeved on the lower pallet and configured to, when the lower pallet moves in the front-back direction relative to the support device, move synchronously with the lower pallet to drive the upper pallet to move in the same direction back and forth relative to the lower pallet, and
    wherein the endless belt is coupled with a first connector fixed on the support device, wherein a lower part of the endless belt is fixedly coupled to the support device by the first connector, and an upper part of the endless belt is fixedly coupled to the upper pallet by a second connector, and wherein the first connector is disposed at a front end of the lower part of the endless belt, and the second connector is disposed at a back end of the upper part of the endless belt.

2. The scanning table of claim 1, wherein the driving device comprises:
    a reversing device;
    a power component disposed at a back end of the scanning table; and
    a transmission shaft disposed along the front-back direction, an axis of the transmission shaft being along the front-back direction,
    wherein a back end of the transmission shaft is coupled to the power component, and a front end of the transmission shaft is coupled to the reversing device, and
    wherein a power is transmitted to the first driving wheel by the reversing device.

3. The scanning table of claim 2, wherein the reversing device comprises:
    a second driving wheel; and
    a third driving wheel cooperated with the second driving wheel,
    wherein an axis of the second driving wheel is in the left-right direction of the scanning table and is coupled circumferentially with the first driving wheel, and wherein an axis of the third driving wheel is in the front-back direction and is coupled to the front end of the transmission shaft.

4. The scanning table of claim 3, wherein both of the second driving wheel and the third driving wheel are spiral bevel gears or straight tooth bevel gears.

5. The scanning table of claim 2, wherein the reversing device comprises a right angle reducer.

6. The scanning table of claim 2, further comprising:
a front connector fixedly coupled with the front end of the opening belt, the front connector being ahead of the first driving wheel along the front-back direction; and
a back connector fixedly coupled with a back end of the opening belt,
wherein a front end of the lower pallet is fixedly coupled with the front connector, and a back end of the lower pallet is fixedly coupled with the back connector.

7. The scanning table of claim 6, wherein the opening belt comprises a front opening belt located in front of the first driving wheel and a back opening belt located behind the first driving wheel, and the front opening belt and the back opening belt are disposed in a same plane above the first driving wheel,
wherein the front connector is fixedly coupled to a front end of the front opening belt, and the back connector is fixedly coupled to a back end of the back opening belt, and
wherein the scanning table further comprises:
a first transmission wheel above the first driving wheel, the first transmission wheel being located below the opening belt and configured to guide the front opening belt to extend upward; and
a second transmission wheel above the first driving wheel, the second transmission wheel being located below the opening belt and configured to guide the back opening belt to extend upward,
wherein the first driving wheel is located between the first transmission wheel and the second transmission wheel and above a portion of the opening belt that is between the front opening belt and the back opening belt.

8. The scanning table of claim 1, further comprising:
a third transmission wheel hinged at a front end of the lower pallet; and
a fourth transmission wheel hinged at a back end of the lower pallet,
wherein a hinge shaft of the third transmission wheel and a hinge shaft of the fourth transmission wheel are in the left-right direction of the scanning table, and
wherein the endless belt is sleeved on the third transmission wheel and the fourth transmission wheel.

9. The scanning table of claim 8, wherein the opening belt comprises a synchronous belt or a chain, and the first driving wheel comprises a synchronous pulley or a chain wheel, and
wherein the endless belt comprises a synchronous belt or a chain, and both of the third transmission wheel and the fourth transmission wheel are synchronous pulleys or chain wheels.

10. The scanning table of claim 1, wherein a length of the opening belt is substantially half of a length of the endless belt.

11. A medical imaging system comprising:
an imaging device configured to scan a region of interest of a subject; and
a scanning table configured to support the subject, the scanning table comprising:
an upper pallet configured to support the subject;
a lower pallet;
a support device configured to support the upper pallet and the lower pallet;
a driving device configured to drive the upper pallet and the lower pallet to move in a front-back direction;
an opening belt configured to drive the lower pallet to move in the front-back direction relative to the support device; and
an endless belt configured to drive the upper pallet to move in the front-back direction relative to the lower pallet,
wherein the opening belt is fixedly coupled with the lower pallet, and the endless belt is fixedly coupled with the upper pallet,
wherein a front end of the opening belt is provided with a first driving wheel coupled to the driving device, and an axis of the first driving wheel is in a left-right direction of the scanning table,
wherein the lower pallet is driven by the first driving wheel to move in the front-back direction relative to the support device,
wherein the endless belt is sleeved on the lower pallet and configured to, when the lower pallet moves in the front-back direction relative to the support device, move synchronously with the lower pallet to drive the upper pallet to move in the same direction back and forth relative to the lower pallet, and
wherein the endless belt is coupled with a first connector fixed on the support device, wherein a lower part of the endless belt is fixedly coupled to the support device by the first connector, and an upper part of the endless belt is fixedly coupled to the upper pallet by a second connector, and wherein the first connector is disposed at a front end of the lower part of the endless belt, and the second connector is disposed at a back end of the upper part of the endless belt.

12. The medical imaging system of claim 11, wherein the driving device comprises:
a reversing device;
a power component disposed at a back end of the scanning table; and
a transmission shaft disposed along the front-back direction, an axis of the transmission shaft being along the front-back direction,
wherein a back end of the transmission shaft is coupled to the power component, and a front end of the transmission shaft is coupled to the reversing device, and
wherein a power is transmitted to the first driving wheel by the reversing device.

13. The medical imaging system of claim 12, wherein the reversing device comprises:
a second driving wheel; and
a third driving wheel cooperated with the second driving wheel,
wherein an axis of the second driving wheel is in the left-right direction of the scanning table and is coupled circumferentially with the first driving wheel, and
wherein an axis of the third driving wheel is in the front-back direction and is coupled to the front end of the transmission shaft.

14. The medical imaging system of claim 13, wherein both of the second driving wheel and the third driving wheel are spiral bevel gears or straight tooth bevel gears.

15. The medical imaging system of claim 11, wherein the scanning table further comprises:

a front connector fixedly coupled with the front end of the opening belt, the front connector being ahead of the first driving wheel along the front-back direction; and
a back connector fixedly coupled with a back end of the opening belt,
wherein a front end of the lower pallet is fixedly coupled with the front connector; and a back end of the lower pallet is fixedly coupled with the back connector.

16. The medical imaging system of claim 15, wherein the opening belt comprises a front opening belt located in front of the first driving wheel and a back opening belt located behind the first driving wheel, the front opening belt and the back opening belt being disposed in a same plane below the first driving wheel,
wherein the front connector is fixedly coupled to a front end of the front opening belt, and the back connector is fixedly coupled to a back end of the back opening belt, and
wherein the scanning table further comprises:
a first transmission wheel above the first driving wheel, the first transmission wheel being located below the opening belt and configured to guide the front opening belt to extend upward; and
a second transmission wheel above the first driving wheel, the second transmission wheel being located below the opening belt and configured to guide the back opening belt to extend upward,
wherein the first driving wheel is located between the first transmission wheel and the second transmission wheel and above a portion of the opening belt that is between the front opening belt and the back opening belt.

17. The medical imaging system of claim 11, wherein the scanning table further comprises:
a third transmission wheel hinged at a front end of the lower pallet; and
a fourth transmission wheel hinged at a back end of the lower pallet,
wherein a hinge shaft of the third transmission wheel and a hinge shaft of the fourth transmission wheel are in the left-right direction of the scanning table, and the endless belt is sleeved on the third transmission wheel and the fourth transmission wheel.

18. The medical imaging system of claim 11, wherein a length of the opening belt is substantially half of a length of the endless belt.

19. A scanning table comprising:
an upper pallet configured to support a subject;
a lower pallet;
a support device configured to support the upper pallet and the lower pallet;
a driving device configured to drive the upper pallet and the lower pallet to move in a front-back direction;
an opening belt configured to drive the lower pallet to move in the front-back direction relative to the support device;
an endless belt configured to drive the upper pallet to move in the front-back direction relative to the lower pallet;
a front connector fixedly coupled with a front end of the opening belt, the front connector being ahead of a first driving wheel along the front-back direction; and
a back connector fixedly coupled with a back end of the opening belt, wherein a front end of the lower pallet is fixedly coupled with the front connector, and a back end of the lower pallet is fixedly coupled with the back connector,
wherein the opening belt is fixedly coupled with the lower pallet, and the endless belt is fixedly coupled with the upper pallet,
wherein the front end of the opening belt is provided with the first driving wheel coupled to the driving device and an axis of the first driving wheel is in a left-right direction of the scanning table, and wherein the lower pallet is driven by the first driving wheel to move in the front-back direction relative to the support device,
wherein the endless belt is sleeved on the lower pallet and configured to, when the lower pallet moves in the front-back direction relative to the support device, move synchronously with the lower pallet to drive the upper pallet to move in the same direction back and forth relative to the lower pallet, and
wherein the driving device comprises: a reversing device, a power component disposed at a back end of the scanning table, and a transmission shaft disposed along the front-back direction, an axis of the transmission shaft being along the front-back direction, wherein a back end of the transmission shaft is coupled to the power component, and a front end of the transmission shaft is coupled to the reversing device, and wherein a power is transmitted to the first driving wheel by the reversing device.

20. The scanning table of claim 19, wherein the endless belt is coupled with a first connector fixed on the support device,
wherein a lower part of the endless belt is fixedly coupled to the support device by the first connector, and an upper part of the endless belt is fixedly coupled to the upper pallet by a second connector, and
wherein the first connector is disposed at a front end of the lower part of the endless belt, and the second connector is disposed at a back end of the upper part of the endless belt.

* * * * *